United States Patent
Costa et al.

(10) Patent No.: US 7,651,865 B2
(45) Date of Patent: Jan. 26, 2010

(54) CONDITIONING SLURRY SAMPLES FOR QUANTITATIVE INSTRUMENTAL ANALYSIS

(75) Inventors: Mario Luis Costa, Hamilton (CA);
John Brian Birks, Toronto (CA);
Chunmin Pu, Mississauga (CA); Kui Xu, Toronto (CA)

(73) Assignee: Superior Plus Inc., Calgary, Alberta (CA)

( * ) Notice: Subject to any disclaimer, the term of this patent is extended or adjusted under 35 U.S.C. 154(b) by 532 days.

(21) Appl. No.: 11/402,946

(22) Filed: Apr. 13, 2006

(65) Prior Publication Data
US 2006/0251560 A1 Nov. 9, 2006

Related U.S. Application Data

(60) Provisional application No. 60/671,085, filed on Apr. 14, 2005.

(51) Int. Cl.
*G01N 1/18* (2006.01)

(52) U.S. Cl. .................... 436/177; 423/321.1

(58) Field of Classification Search .............. 436/177
See application file for complete search history.

(56) References Cited

U.S. PATENT DOCUMENTS

| | | | | | |
|---|---|---|---|---|---|
| 3,637,079 | A | * | 1/1972 | Strub | 210/794 |
| 6,134,952 | A | * | 10/2000 | Garver et al. | 73/61.71 |
| 7,014,779 | B1 | * | 3/2006 | Kirchner | 210/739 |
| 2003/0118503 | A1 | * | 6/2003 | Pu et al. | 423/478 |

* cited by examiner

*Primary Examiner*—Yelena G Gakh
*Assistant Examiner*—Dirk Bass
(74) *Attorney, Agent, or Firm*—Michael I. Stewart; Sim & McBurney

(57) ABSTRACT

A method and system to consistently and automatically conditioning and delivering a solid-free liquid (filtrate) sample suitable for instrumental analysis is disclosed. A slurry, preferably a slurry produced by a sub-atmospheric pressure chlorate dioxide generating process, is fed through a filter to remove the solid phase and to provide the liquid phase on the downstream side of the filter, where the concentration of at least one dissolved component is determined.

7 Claims, 2 Drawing Sheets

Slurry Conditioning System - Schematic

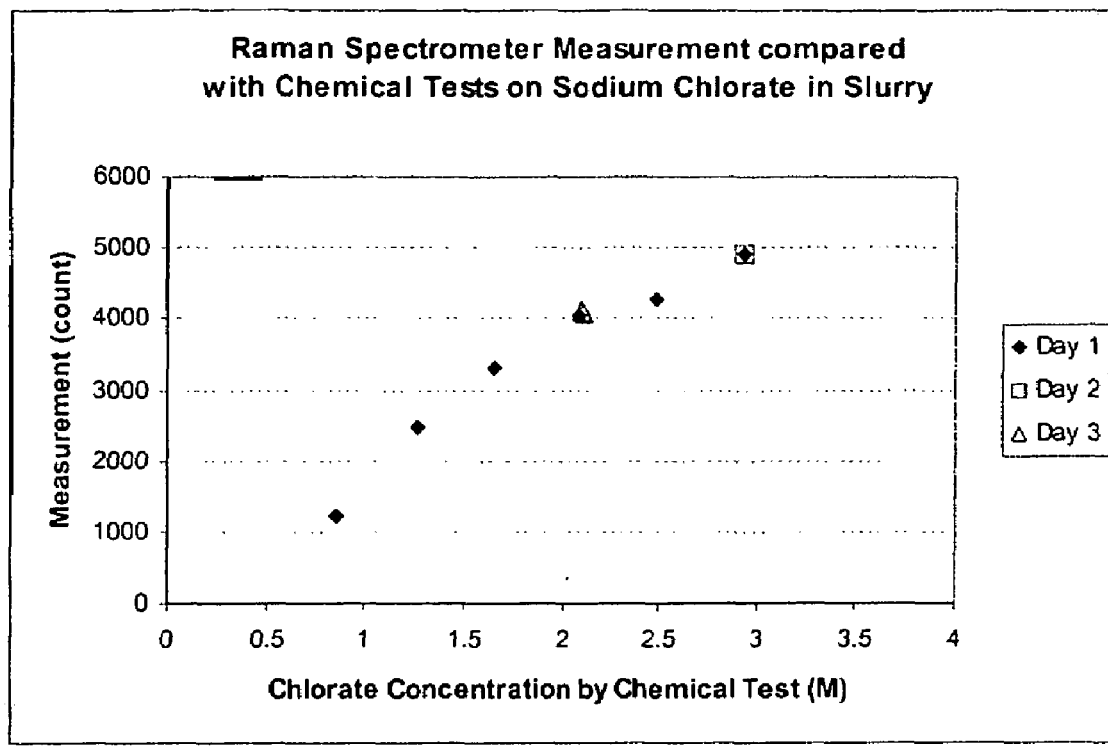
Figure 1: Field test data of instrumental analysis compared with chemical tests on sodium chlorate in the reactor liquor

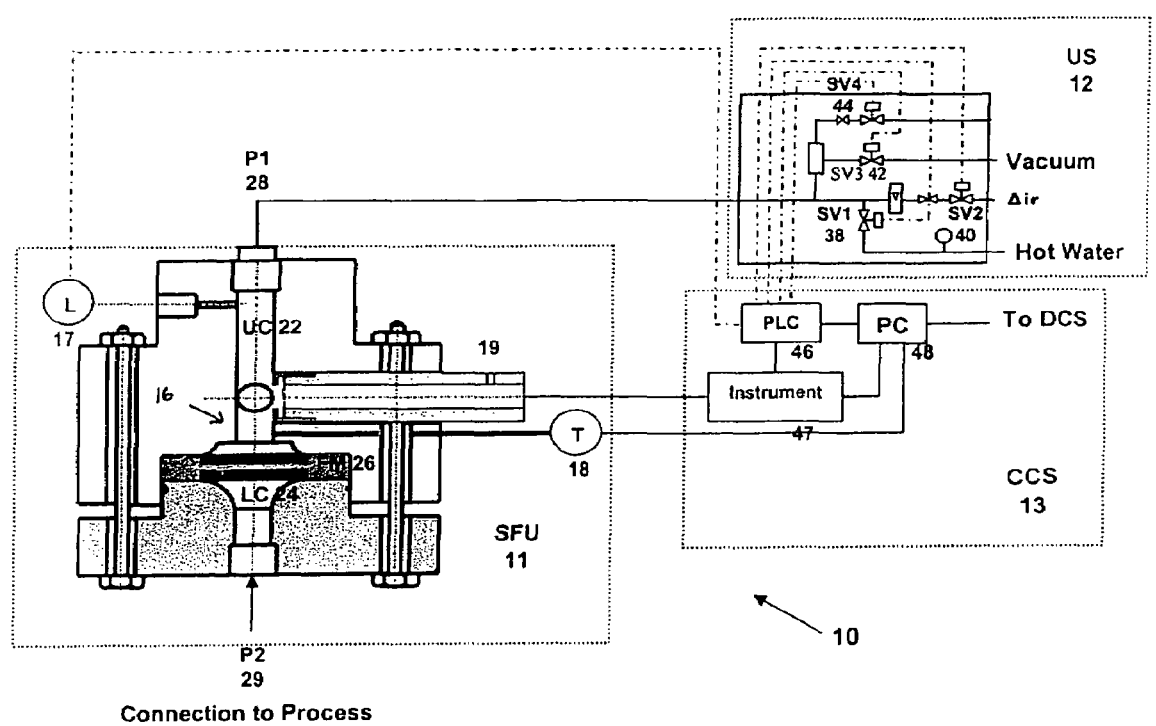
Figure 2: Slurry Conditioning System - Schematic

US 7,651,865 B2

CONDITIONING SLURRY SAMPLES FOR QUANTITATIVE INSTRUMENTAL ANALYSIS

FIELD OF INVENTION

The present invention is concerned with rendering slurry samples suitable for instrumental analysis.

BACKGROUND TO THE INVENTION

The vast majority of chemical processes to generate chlorine dioxide currently in commercial use in pulp mills take place under sub-atmospheric conditions. In such processes, chlorine dioxide is generated by reducing sodium chlorate using a reducing agent, such as methanol or hydrogen peroxide, in an aqueous acid reaction medium containing sulfuric acid maintained at its boiling point under a sub-atmospheric pressure. The reaction medium in such processes is a slurry with a solids content commonly ranging from about 10 to about 30% w/w. The two major parameters in terms of the concentration control in the reactor, namely chlorate molarity and titratable acidity, are normally maintained within target bands no wider than +/−about 0.2 M and +/−about 0.2 N, respectively. Such control targets are accomplished based on analytical results of chemical tests performed manually by plant operators.

Being able to continuously monitor liquor composition is desirable beyond the obvious manpower savings. The accuracy and precision of process control that would be achieved by means of on-line measurement would ultimately lead to higher reaction efficiency and lower chemical consumptions. But all known attempts to meet the above analytical requirements without human intervention have not been successful or not in sustainable and reliable services. One of the reasons is the difficulty inherent to the sampling of hot and saturated slurry-type process streams.

SUMMARY OF INVENTION

The present invention provides a method and system for consistently and automatically conditioning and delivering a solids-free liquid (filtrate) sample suitable for instrumental analyses. While the present invention is described in detail with respect to slurries from chlorine dioxide generating plants, it will be clear to a person skilled in the art that the principles described herein are applicable to all types of slurries encountered in industrial processes.

In accordance with one aspect of the present invention, there is provided a method of measuring the concentration of at least one dissolved component in the liquid phase of a slurry, which comprises providing an analytical unit comprising an inlet chamber for said slurry in communication with an inlet, a filtration medium for removing the solid phase from the slurry located downstream of the inlet chamber, and a chamber downstream of the filter in communication with an outlet, feeding said slurry to said inlet, then through said filtration medium to separate said solid phase from the liquid phase with the liquid phase passing into the chamber until a predetermined amount of said liquid phase has entered said chamber, and measuring the concentration of the at least one dissolved component in the liquid phase in said chamber.

In accordance with another aspect of the present invention, there is provided an analytical system for measuring the concentration of at least one dissolved component in the liquid phase of a slurry, which comprises a slurry filtration unit comprising a filtration cell comprising an inlet for the slurry to a slurry chamber, a filtration medium for separation of the solid phase from the slurry, and a liquid phase chamber downstream of said filtration medium and having an outlet therefrom, said liquid phase chamber having a liquid level sensor and a concentration measurement probe in operable association therewith, a utility system in operable relationship with said slurry filtrate unit for selectively applying compressed air, water and vacuum to the outlet from said slurry filtration unit, and a control/communication system in operable relationship with said slurry filtration unit and said utility system for controlling the operation of the analytical system in response to a pre-programmed set of commands

BRIEF DESCRIPTION OF DRAWING

FIG. 1 is a graphical representation of experiments conducted comparing the concentration of sodium chlorate in a chlorine dioxide-generating reaction medium, measured by Raman spectrometer in comparison to chemical tests; and FIG. 2 contains a schematic illustration of a slurry conditioning system provided in accordance with a preferred embodiment of the invention and comprising a slurry filtration unit (SFU), a utility system (US) and a control/communication system (CCS).

GENERAL DESCRIPTION OF INVENTION

Referring to FIG. 2, a slurry conditioning system 10 includes a slurry filtration unit (SFU) 11, a utility system (US) 12 and a control/communication system (CCS) 13. The SFU is a filtration cell (FC) 16, equipped with a level sensor 17, a temperature sensor 18 and an instrument probe 19.

The FC filtration cell 16 consists of an upper chamber (UC) 22 separated from a lower chamber (LC) 24 by a filtration medium (FM) 26. The filtration medium 26 may be of variable size and material of construction, depending on the nature of the slurry to be processed. An upper port (P1) 28 is connected to the utility assembly 12. Other ports are provided for the level sensor 17, temperature sensor 18 and instrument probe 19. A lower port (P2) 29 connects the lower chamber 24 to the process from which the slurry to be tested is taken.

This unit 11 may be used to introduce a probe of any kind for instrumental analyses of the filtered sample, such as IC (ion chromatography), Raman spectroscopy, FT-NIR (Fourier Transform-Near Infra Red) or the like.

The utility system 12 comprises several solenoid valves, namely hot water SV1 38, compressed air SV2 40, vacuum SV3 42 and vacuum relief SV4 44. The arrangement of all connections is to at least minimize and preferably eliminate chances to leave residual water in the cell 16 which could later dilute the filtered sample and result in errors. This consideration is particularly important when the sample volume is to be reduced as much as possible.

In operation, vacuum can be used to create a pressure differential and render filtrate free of solids. The incoming slurry stream via P2 29 may be forced through the filtration media FM 26 in its entirety (called dead end filtration). The method of this invention generally proceeds in cycles involving a number of steps, namely 1) air blow, 2) water washing, 3) air drying, 4) filtration under vacuum, 5) vacuum relief and 6) measurement. The steps 1 to 3 may be repeated more than once should difficulty in filter medium cleaning be encountered. The duration of each step as well as the temperature and pressure conditions in each step are determined based on the characteristics of each slurry treated. A representative Example appears below.

In the approach of applying a vacuum as driving force for filtration, as the filtrate level rises high enough to reach the level sensor L 17, the program in a Programmable Logic Controller (PLC) 46, closes the vacuum valve SV3 42, marking the end of filtration. While the filtrate comes to the upper chamber 22 that is at sub-atmospheric pressure, dissolved gas (chlorine dioxide) is disengaged from the liquid phase, forming bubbles, exerting serious interruptions to the analysis. It has been found that the vacuum can be released to a certain degree by opening SV4 44 for a given time until gas bubbles disappear and the gas phase interference is eliminated.

Depending on the particular slurry being conditioned, water and air temperature are also critical parameters. If no limitation exists, any available temperature in the 10° to 70° C. [see 80° C. below] range may be used. However, for chlorine dioxide generator liquor, it was observed that crystallization can take place in the saturated liquid should the filtrate temperature fall below 40° C. Strictly speaking, the phase diagram has a change at temperature 32° C. below which sodium sulphate decahydrate would precipitate. Due to the reversed relationship of solubility versus temperature when the temperature is above 32° C., the filtrate at its usually initial temperature of 70° C. can remain clear until it cools down to near or below this critical temperature related to the phase change.

From the standpoint of promoting the filtration rate by reducing the slurry viscosity, or preventing the formation of decahydrate fine particulates in the filtered sample, it is essential to maintain the filtration cell temperature well above 40° C.

It is particularly challenging to accomplish such thermostatic conditions when performing vacuum filtration due to the cooling effect of water vaporization in UC 22.

For the reasons expressed above, the preferred embodiment employs hot water with a temperature in the range of about 50° to about 80° C. In cases where it is difficult to maintain the cell 16 at the temperature needed to prevent crystallization, it may be necessary to surround the SFU 11 with an enclosure and supply hot air or heating.

The PLC 46 controls the sequence of operations based on the program and signals received. The output from PLC 46 are signals to activate/deactivate individual solenoid valves. The specific instrument probe starts measurement as the instrument 47 receives a trigger from PLC 46. The signal of the probe is sent to a site computer PC 48 where it is converted to a standard signal that is transmitted to the DCS (Distributed Control System).

EXAMPLE

This Example illustrates a conditioning cycle for the filtration system described in reference to FIG. 2 and equipped with a Raman laser probe that transmits spectra to Raman spectrometer as the analytical instrument.

The conditioning cycle proceeds in accordance with Table I below:

TABLE I

| Step | Action | Typical duration (sec) | Input Level | SV1 (water) | SV2 (air) | SV3 (vacuum) | SV4 (Vacuum relief) | Trigger |
|---|---|---|---|---|---|---|---|---|
| 1 | Air blow | 20 | open | close | open | close | close | inactive |
| 2 | Water washing | 120 | open | open | close | close | close | inactive |
| 3 | Air drying | 120 | open | close | open | close | close | inactive |
| 4 | Vacuuming/Filtering | L controlled | close | close | close | open | close | inactive |
| 5 | Vacuum relief | 30 | close | close | close | close | open | inactive |
| 6 | Stabilization | 30 | close | close | close | close | close | inactive |
| 7 | Raman measurement | 300 | close | close | close | close | close | active |
| | Next cycle starts | | | | | | | |

Operating Conditions:
Hot water temperature: 70° C.
Hot water pressure: 15 psig
Compressed air pressure: 20 psig
Compressed air temperature: Room temperature
Vacuum (maximum): 25 in.Hg
Vacuum relief low limit: 10 to 15 in.Hg A comparison was made of instrumental analysis carried out as described above to provide Raman spectrometer measurements with chemical tests on the sodium chlorate concentration in a slurry from a chlorine dioxide generator. The results are presented graphically in FIG. 1, from which it can be seen that there is close correlation of the data.

SUMMARY OF DISCLOSURE

In summary of this disclosure, the present invention provides a novel system and procedure for consistently and automatically conditioning slurries and obtaining good filtrate sample for instrumental analyses. Modifications are possible within the scope of the invention.

What we claim is:

1. A method of measuring the concentration of at least one dissolved component selected from the group consisting of sodium chlorate and sulfuric acid present in the liquid phase of a slurry of crystalline sodium sulfate in a spent reaction medium from a chlorine dioxide generating process in which chlorine dioxide is generated by reducing sodium chlorate with a reducing agent in an aqueous reaction medium containing sulfuric acid at the boiling point of the reaction medium under a sub-atmospheric pressure, which comprises:

providing an analytical unit having a vertical orientation defining a straight line flow path from a lower inlet to an upper outlet and comprising a lower inlet chamber for said slurry in communication with said lower inlet, a filtration medium for removing the crystalline sodium sulfate from the slurry located downstream of the lower inlet chamber and transverse to said flow path, and an upper chamber downstream of the filtration medium in communication with said upper outlet;

applying vacuum to said upper outlet to draw said slurry into said lower inlet and thence into said lower inlet chamber, then through said filtration medium to separate said crystalline sodium sulfate from the liquid phase with the filtration liquid phase passing through the filtration medium into said upper chamber until a predetermined amount of said liquid phase has entered said upper chamber; and measuring the concentration of the at least one dissolved component in the liquid phase in said upper chamber.

2. The method of claim 1 wherein said vacuum application is preceded by the steps of:

applying compressed air to said upper outlet to remove from the analytical unit any liquid and solid remaining from a prior measurement, washing the filtration medium, the upper chamber and the lower inlet chamber by the flowing of wash water from the upper outlet to the lower inlet, and air drying the upper chamber, the filtration medium and the lower inlet chamber by flowing compressed air from the upper outlet to the lower inlet.

3. The method of claim 2, wherein, following said vacuum application, the vacuum application to the upper outlet is terminated and is released.

4. The method of claim 1 wherein the concentration of sodium chlorate in the liquid phase is measured.

5. The method of claim 1 wherein the concentration of sulfuric acid in the liquid phase is measured.

6. The method of claim 1 wherein the concentration of the at least one dissolved component determined is used to control the concentration of that component in the reaction medium within a predetermined range.

7. The method of claim 1 wherein, following the vacuum application to said upper outlet to feed said slurry to said lower inlet into said lower inlet chamber and then through said filtration medium to separate crystalline sodium sulfate from the liquid phase with the filtered liquid phase passing through the filtration medium into said upper chamber until a predetermined amount of said liquid phase has entered said upper chamber, vacuum is applied to said upper outlet at a level which does not draw liquid phase into the upper chamber, thereby to release any dissolved gaseous chlorine dioxide from the liquid phase in said upper chamber.

* * * * *